(12) United States Patent
Othel-Jacobsen

(10) Patent No.: US 12,636,432 B2
(45) Date of Patent: May 26, 2026

(54) NEEDLE AND HOUSING

(71) Applicant: UNOMEDICAL A/S, Lejre (DK)

(72) Inventor: Erik Othel-Jacobsen, Snekkersten (DK)

(73) Assignee: Unomedical A/S, Lejre (DK)

( * ) Notice: Subject to any disclaimer, the term of this patent is extended or adjusted under 35 U.S.C. 154(b) by 955 days.

(21) Appl. No.: 17/727,137

(22) Filed: Apr. 22, 2022

(65) Prior Publication Data

US 2022/0339352 A1 Oct. 27, 2022

Related U.S. Application Data

(63) Continuation of application No. PCT/EP2022/060650, filed on Apr. 22, 2022.

(60) Provisional application No. 63/179,002, filed on Apr. 23, 2021.

(51) Int. Cl.
A61M 5/158 (2006.01)
A61M 5/142 (2006.01)

(52) U.S. Cl.
CPC ........ A61M 5/158 (2013.01); A61M 5/14248 (2013.01); *A61M 2005/14252* (2013.01); *A61M 2005/1585* (2013.01)

(58) Field of Classification Search
CPC .............. A61M 5/158; A61M 5/14248; A61M 2005/14252; A61M 2005/1585; A61M 2005/341; A61M 5/329
See application file for complete search history.

(56) References Cited

U.S. PATENT DOCUMENTS

| 11,071,823 B2 | 7/2021 | Cassim |
|---|---|---|
| 11,197,954 B2 | 12/2021 | Staub et al. |
| 11,202,858 B2 | 12/2021 | Yigal et al. |
| 11,229,753 B2 | 1/2022 | Cote et al. |
| 11,253,653 B2 | 2/2022 | Hostettler et al. |
| 11,260,172 B2 | 3/2022 | Barmaimon et al. |
| 11,471,592 B2 | 10/2022 | Searle et al. |
| 11,490,831 B2 | 11/2022 | Limaye et al. |
| 11,701,300 B2 | 7/2023 | Lanier, Jr. et al. |
| 11,702,233 B2 | 7/2023 | Grant et al. |

(Continued)

FOREIGN PATENT DOCUMENTS

| EP | 0937475 A2 | 8/1999 |
|---|---|---|
| EP | 3574943 B1 | 6/2021 |

(Continued)

OTHER PUBLICATIONS

European Patent Office; Notification of Transmittal of the ISR and the WO of the ISA, Or The Declaration; Date of Mailing: Aug. 16, 2022; pp. 1.

(Continued)

*Primary Examiner* — James D Ponton
(74) *Attorney, Agent, or Firm* — TAFT STETTINIUS HOLLISTER LLP; Ryan O. White; Derek B. Lavender

(57) ABSTRACT

An inserter assembly that has a base, a needle, an inner part that selectively transitions the needle from a retracted position substantially within the base to an extended position where at least a portion of the needle extends outside of the base, and an insertion angle component. As the inner part of the inserter assembly transitions from the retracted position to the extended position, the needle is at least partially deflected by the insertion angle component.

11 Claims, 11 Drawing Sheets

(56) References Cited

U.S. PATENT DOCUMENTS

| | | | |
|---|---|---|---|
| 11,738,140 B2 | 8/2023 | Pananen et al. | |
| 11,744,937 B2 | 9/2023 | Searle et al. | |
| 11,806,505 B2 | 11/2023 | Pananen et al. | |
| 11,819,660 B2 | 11/2023 | Bar-El et al. | |
| 11,890,088 B2 | 2/2024 | Limaye et al. | |
| 11,904,136 B2 | 2/2024 | Constantineau et al. | |
| 11,980,738 B1 | 5/2024 | Lipman et al. | |
| 11,998,328 B2 | 6/2024 | Jager | |
| 11,998,727 B2 | 6/2024 | Cote et al. | |
| 12,012,241 B2 | 6/2024 | Lanigan et al. | |
| 12,023,465 B2 | 7/2024 | Constantineau et al. | |
| 2006/0013710 A1 | 1/2006 | Lee | |
| 2014/0207104 A1* | 7/2014 | Vouillamoz | A61M 5/158 |
| | | | 604/179 |
| 2018/0280608 A1 | 10/2018 | Gillett et al. | |
| 2018/0333533 A1 | 11/2018 | Levine et al. | |
| 2019/0336679 A1* | 11/2019 | Staub | A61M 5/158 |
| 2020/0030529 A1 | 1/2020 | DiPerna et al. | |
| 2021/0162117 A1 | 6/2021 | Michaud et al. | |
| 2021/0213195 A1 | 7/2021 | Constantineau et al. | |
| 2021/0236722 A1 | 8/2021 | Bar-El et al. | |
| 2021/0308367 A1 | 10/2021 | Searle et al. | |
| 2021/0321914 A1 | 10/2021 | Brister et al. | |
| 2021/0353911 A1 | 11/2021 | Cole | |
| 2022/0063847 A1 | 3/2022 | Lanigan et al. | |
| 2022/0241497 A1 | 8/2022 | Burren et al. | |
| 2022/0265210 A1 | 8/2022 | Cargill et al. | |
| 2022/0347388 A1 | 11/2022 | Norton et al. | |
| 2022/0362458 A1 | 11/2022 | Schrul et al. | |
| 2022/0362459 A1 | 11/2022 | Kamen et al. | |
| 2022/0370708 A1 | 11/2022 | Gillett et al. | |
| 2022/0379019 A1 | 12/2022 | Lanigan et al. | |
| 2022/0379022 A1 | 12/2022 | Meglan et al. | |
| 2023/0211082 A1 | 7/2023 | Kuehn et al. | |
| 2023/0233758 A1 | 7/2023 | Gregory et al. | |
| 2023/0330331 A1 | 10/2023 | Pananen et al. | |
| 2024/0100251 A1 | 3/2024 | Constantineau et al. | |
| 2024/0115155 A1 | 4/2024 | Limaye et al. | |

FOREIGN PATENT DOCUMENTS

| | | |
|---|---|---|
| EP | 2155299 B1 | 1/2022 |
| EP | 3988147 A1 | 4/2022 |
| EP | 4000668 A1 | 5/2022 |
| EP | 4008377 A1 | 6/2022 |
| EP | 4035707 A1 | 8/2022 |
| EP | 3570908 B1 | 11/2023 |
| EP | 4301433 A1 | 1/2024 |
| EP | 3762068 B1 | 2/2024 |
| EP | 3474927 B1 | 6/2024 |
| NO | 2013016376 A2 | 1/2013 |
| WO | 2020097552 A1 | 5/2020 |
| WO | 2022171846 A1 | 8/2022 |
| WO | 2022186887 A1 | 9/2022 |

OTHER PUBLICATIONS

European Patent Office; International Search Report of corresponding application PCT/EP2022/060650; Date of mailing: Aug. 16, 2022; pp. 2.

European Patent Office; From the International Searching Authority; Written Opinion of the ISA of corresponding application PCT/EP2022/060650; pp. 1-3; Date of Mailing: Aug. 16, 2022.

JP Office Action; Japan Patent Office; Application No. 2023-564590; Jan. 27, 2026; 9 pages.

CN Office Action; Chinese National Intellectual Property Administration; CN Application No. 20228002988038; Mar. 31, 2026; 10 pages.

* cited by examiner

NEEDLE AND HOUSING

CROSS-REFERENCE TO RELATED DISCLOSURES

The present disclosure is a continuation of International Application No. PCT/EP2022/060650 filed on Apr. 22, 2022 and claims the benefit of U.S. Provisional Application No. 63/179,002 filed on Apr. 23, 2021, the contents of which are incorporated herein in entirety.

FIELD OF THE DISCLOSURE

The present disclosure relates to mechanism for inserting a needle and more specifically to a mechanism that deforms the needle as part of the insertion process.

BACKGROUND OF THE DISCLOSURE

Inserter mechanisms are frequently used to facilitate insertion of a needle and/or cannula into a user to further distribute fluid into, or remove fluid from, the body of the user. Typically, the needle is positioned within the inserter mechanism in a retracted position and has a substantially linear dimension. The inserter may be activated wherein the needle is extended axially along a longitudinal axis of the needle into soft tissue of the user. The inserted needle or cannula typically remains in the user for a period of time. Accordingly, the bulky inserter mechanism is often removed after the needle and/or cannula is inserted to reduce the size and weight of the device while in use. After the needle and/or cannula is inserted into the user, it is often fluidly coupled to a fluid delivery or retention device.

SUMMARY

One embodiment is an inserter assembly that has a base, a needle, an inner part configured to selectively transition the needle from a retracted position substantially within the base to an extended position where at least a portion of the needle extends outside of the base, and an insertion angle component. In this embodiment, as the inner part transitions from the retracted position to the extended position, the needle is at least partially deflected by the insertion angle component.

In one example of this embodiment, the inner part rotates about a rotation axis to transition the needle from the retracted position to the extended position. In another example the inner part is rotationally coupled to the base about a rotation axis. As part of this example, the inner part is coupled to the needle such that rotation of the inner part about the rotation axis moves the needle about the rotation axis.

In another example of this embodiment the needle is elastically deformable to fit within the base and deflect through contact with the insertion angle component as the needle transitions from the retracted position to the extended position. In part of this example, the needle maintains a substantially linear configuration as it extends outside of the base.

Yet another example includes a base fluid channel defined partially in the base. This example may have an inner fluid channel defined in the inner part, wherein the base fluid channel is fluidly coupled to the inner fluid channel. Further, the inner fluid channel is fluidly coupled to a needle fluid channel, wherein fluid from the base fluid channel is directed partially through the inner fluid channel of the inner part and into the needle fluid channel of the needle regardless of a rotation angle of the inner part relative to the base about a rotation axis. In another part of this example, the base fluid channel is fluidly coupled to the inner fluid channel at least partially along the rotation axis. One aspect of this part includes a circular seal positioned between the inner part and the base to fluidly seal a transition between the base fluid channel and the inner fluid channel regardless of the angular orientation of the inner part relative to the base about the rotation axis.

Yet another example of this embodiment has a top assembly that is selectable to transition the needle from the retracted position to the extended position. As part of this example, the top assembly has a driver, a lid, a release mechanism, and a spring positioned there between. The driver is rotationally fixed to the inner part when the top assembly is coupled to the inserter assembly. Further, the top assembly is removable from the base and inner part. In another aspect of this example, the top assembly has a loaded configuration wherein the spring applies a rotational bias to the driver relative to the lid, wherein when the release mechanism is released, the driver rotates relative to the lid about the rotation axis thereby rotating the inner part and transitioning the needle from the retracted position to the extended position.

In another example of this embodiment, the needle is configured to deliver fluid from the base fluid channel to a distal tip of the needle when in the extended position. In yet another example, the base defines a base fluid channel fluidly coupled to the needle to provide fluid thereto, the base fluid channel configured to be fluidly coupled to a fluid delivery device.

In yet another example of this embodiment, the insertion angle component is removable from the base. In one part of this example a plurality of different insertion angle components are coupleable to the base to provide a selectable insertion angle of the needle in the extended position based on the particular insertion angle component coupled to the base.

In another example of this embodiment, the insertion angle component is movable to alter an insertion angle of the needle in the extended position. In another example, the inner part rotates about a rotation axis to retract the needle from the extended position to the retracted position. In yet another example, the degree of rotation of the inner part relative to the base is variable and alters an insertion depth of the needle in the extended position.

In one example of this embodiment, the insertion angle component angles the needle about thirty degrees relative to a surface plane of the base. One part of this example includes a filter in one or more of the base fluid channel, the inner fluid channel, and the needle fluid channel.

In another example, in the extended position the needle extends about three to four millimeters from the base. In yet another example, a rotary actuator rotates the inner part relative to the base to transition the needle from a retracted position to an extended position. As part of this example, the rotary actuator is coupled to gears to rotate the inner part.

Another example of this embodiment includes a second needle coupled to the inner part wherein transitioning the inserter assembly from the retracted position to the extended position extends at least a portion of the second needle outside of the base.

Another embodiment of this disclosure is an inserter assembly that has a base housing a needle and an inserter, the needle being repositionable by the inserter between a retracted position and an extended position. In this embodiment, at least a portion of the needle has an arc-shaped orientation in the retracted position and a substantially linear orientation in the extended position.

In one example of this embodiment the inserter comprises an inner part that rotates about a rotation axis to transition the needle from the retracted position to the extended position. As part of this example the inner part is rotationally coupled to the base about a rotation axis. Further, the inner part is coupled to the needle such that rotation of the inner part about the rotation axis moves the needle about the rotation axis.

In another example of this embodiment, the needle is elastically deformable to fit within the base and deflect as the needle transitions from the retracted position to the extended position.

As one part of this example, the needle maintains a substantially linear configuration as it extends outside of the base.

Another example of this embodiment has a base fluid channel defined partially in the base. Part of this example includes an inner fluid channel defined in an inner part, wherein the base fluid channel is fluidly coupled to the inner fluid channel. In another part of this example, the inner fluid channel is fluidly coupled to a needle fluid channel, wherein fluid from the base fluid channel is directed partially through the inner fluid channel of the inner part and into the needle fluid channel of the needle regardless of a rotation angle of the inner part relative to the base about a rotation axis. Further, the base fluid channel is fluidly coupled to the inner fluid channel at least partially along the rotation axis. This example may include a circular seal positioned between the inner part and the base to fluidly seal a transition between the base fluid channel and the inner fluid channel regardless of the angular orientation of the inner part relative to the base about the rotation axis.

Yet another example of this embodiment includes a top assembly that is selectable to transition the needle from the retracted position to the extended position. In one part of this example, the top assembly comprises a driver, a lid, a release mechanism, and a spring positioned there between. In another part of this example, the driver is rotationally fixed to the inner part when the top assembly is coupled to the inserter assembly. In this configuration the top assembly is removable from the base and inner part. In one part of this example, the top assembly has a loaded configuration wherein the spring applies a rotational bias to the driver relative to the lid, wherein when the release mechanism is released, the driver rotates relative to the lid about the rotation axis thereby rotating the inner part and transitioning the needle from the retracted position to the extended position.

In yet another example of this embodiment the needle is configured to deliver fluid from a base fluid channel to a distal tip of the needle when in the extended position. In one example the base defines a base fluid channel fluidly coupled to the needle to provide fluid thereto, the base fluid channel configured to be fluidly coupled to a fluid delivery device.

In another example an insertion angle component is removable from the base. In one part of this example a plurality of different insertion angle components are couple-able to the base to provide a selectable insertion angle of the needle in the extended position based on the particular insertion angle component coupled to the base.

Yet another example of this embodiment includes an insertion angle component that is movable to alter an insertion angle of the needle in the extended position.

Another example includes an inner part that rotates about a rotation axis to retract the needle from the extended position to the retracted position. In part of this example the degree of rotation of the inner part relative to the base is variable and alters an insertion depth of the needle in the extended position.

Yet another example of this embodiment includes an insertion angle component that angles the needle about thirty degrees relative to a surface plane of the base. Another example has a filter positioned to filter fluid going into the needle. In another example in the extended position the needle extends about three to four millimeters from the base.

Another example includes a rotary actuator that transitions the needle from the retracted position to the extended position. In one part of this example the rotary actuator is coupled to gears.

Another example of this embodiment includes a second needle wherein transitioning from the retracted position to the extended position extends at least a portion of the second needle outside of the base.

BRIEF DESCRIPTION OF THE DRAWINGS

The above-mentioned aspects of the present disclosure and the manner of obtaining them will become more apparent and the disclosure itself will be better understood by reference to the following description of the embodiments of the disclosure, taken in conjunction with the accompanying drawings, wherein:

FIG. 8b is a top view of a portion of the inserter assembly of FIG. 8a;

Corresponding reference numerals are used to indicate corresponding parts throughout the several views.

DETAILED DESCRIPTION

The embodiments of the present disclosure described below are not intended to be exhaustive or to limit the disclosure to the precise forms in the following detailed description. Rather, the embodiments are chosen and described so that others skilled in the art may appreciate and understand the principles and practices of the present disclosure.

Figure 1:
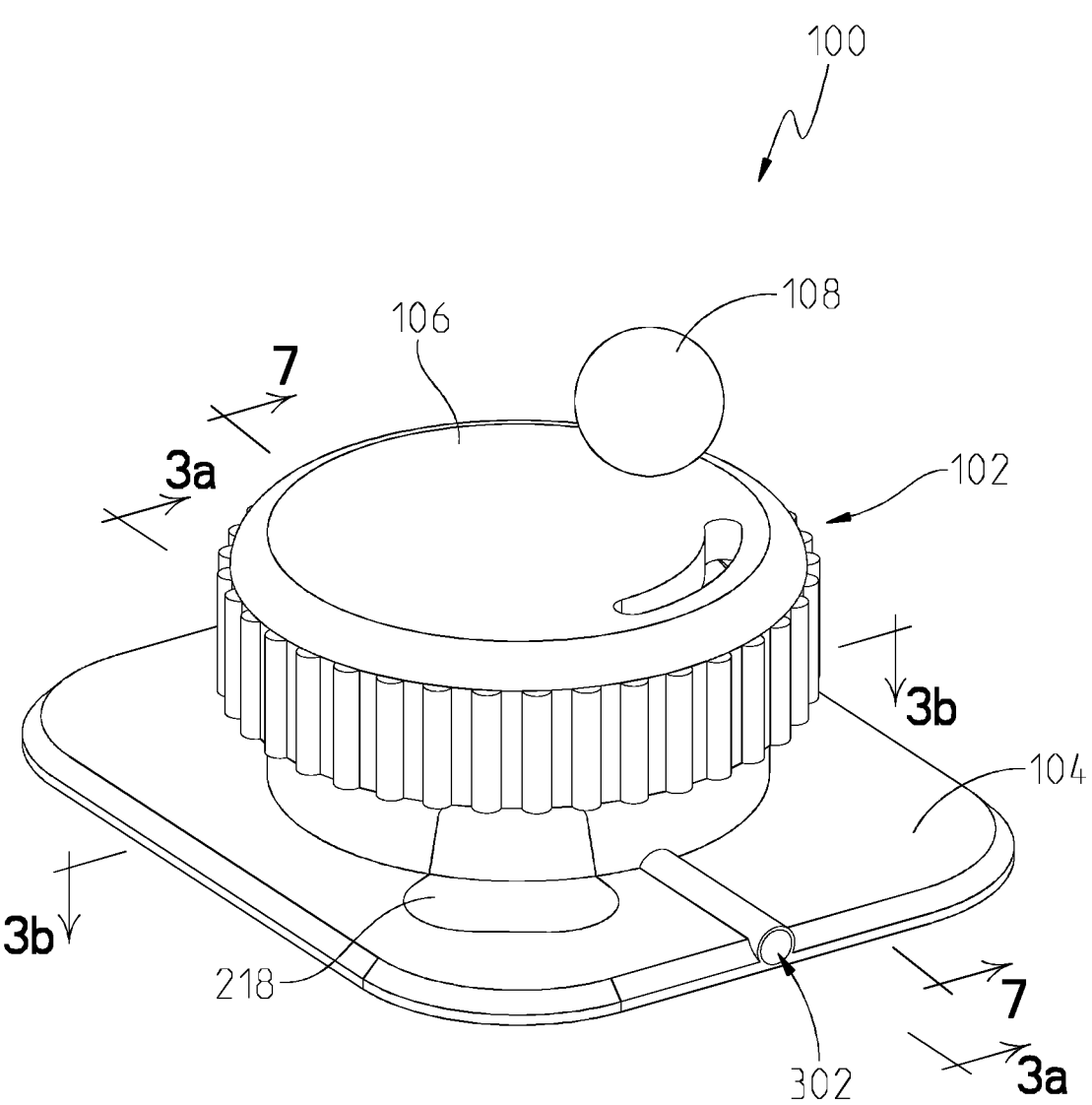
FIG. 1 is an elevated perspective view of one embodiment of an inserter assembly.

Referring to FIG. 1, one embodiment of an inserter assembly 100 is illustrated. The inserter assembly 100 may have a top assembly 102 that is selectively coupleable to a base 104. The top assembly 102 may have a lid 106 and a release mechanism 108 among other components that will be discussed with more detail herein. The base 104 may be configured to be coupled to a user through adhesive or the like so a needle 204 (see FIG. 2) may be selectively positioned in the soft tissue of the user.

Figure 2:
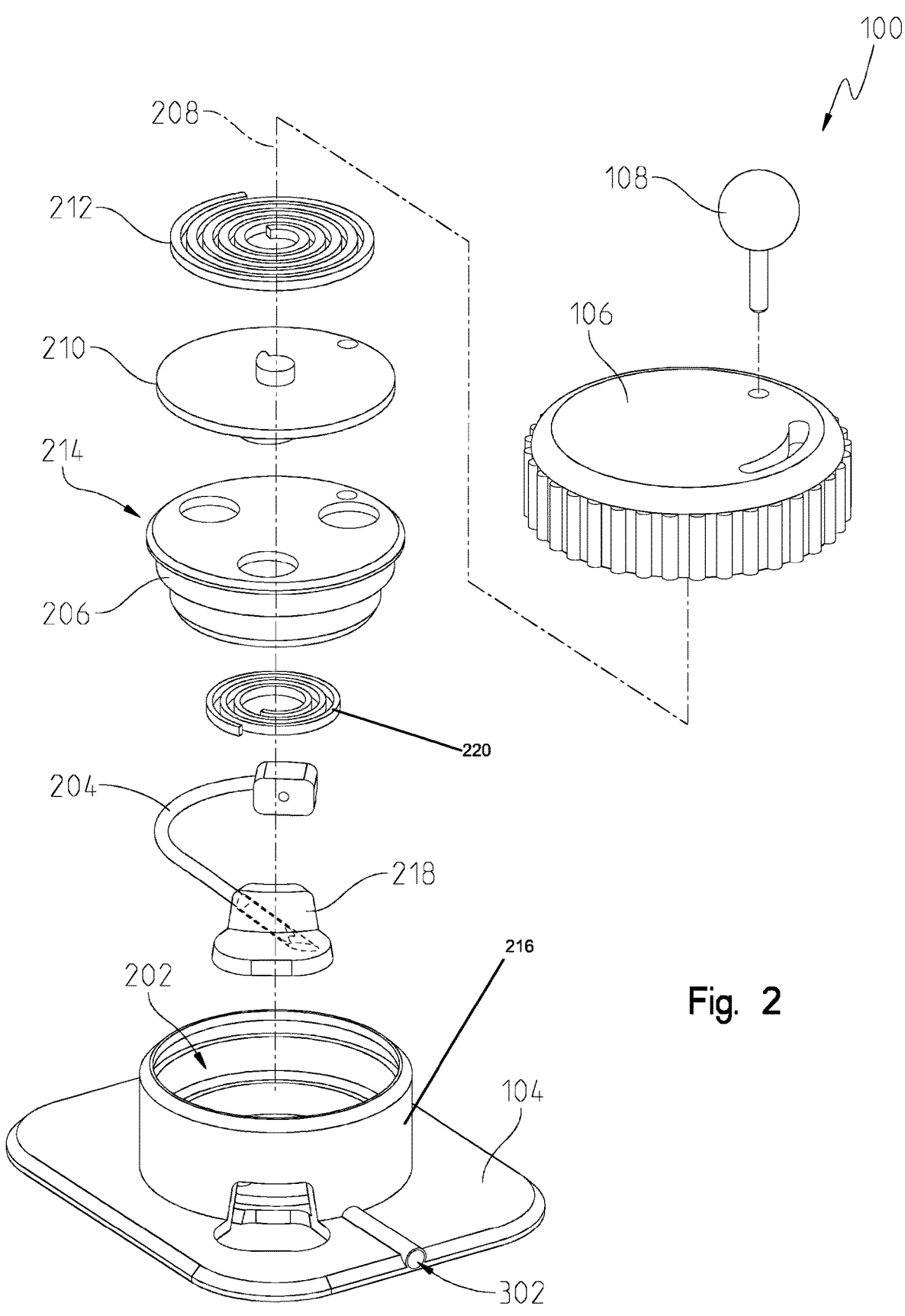
FIG. 2 is an expanded view of the inserter assembly of FIG. 1.

Referring now to FIG. 2, an exploded view of the components of the inserter assembly 100 is illustrated. More specifically, the lid 106 of the top assembly 102 may at least partially cover a cavity 202 created by the base 104 when coupled thereto. At least partially within the cavity 202 may be a needle 204 and an inner part 206 among other things. The inner part 206 may be configured to selectively rotate within the cavity 202 of the base 104 about a rotation axis 208 relative to the base 104. Further, the needle 204 may be coupled to the inner part 206 wherein rotation of the inner part 206 causes movement of the needle 204 as well.

The top assembly 102 may comprise a driver 210 and spring 212 positioned within the lid 106. The driver 210 may be selectively rotatable relative to the lid 106 about the rotation axis 208 when coupled to the base 104. In one aspect of this disclosure, the spring 212 may be loaded to provide a rotation force on the driver 210 relative to the lid 106. The release mechanism 108 may be selectively coupled to the driver 210 to substantially prevent the driver 210 from rotating relative to the lid 106. However, when the release mechanism 108 is removed, the loaded spring 212 may rotate the driver 210 relative to the lid 106.

In one aspect of this disclosure, the driver 210 and inner part 206 may have corresponding features 214 wherein the driver 210 is rotationally locked with the inner part 206 when the top assembly 102 is coupled to the base 104. The corresponding features 214 may be any feature that rotationally locks the driver 210 to the inner part 106 when the top assembly 102 is coupled to the base 104. In the example of FIG. 2, the corresponding features are circular indentations on the surface of the inner part 206 and corresponding circular extrusions on the driver 210. In this configuration, when the top assembly 102 is coupled to the base 104, the circular extrusions of the driver 210 are positioned at least partially within the circular indentations of the inner part 206, thereby preventing substantial relative rotation between the driver 210 and the inner part 206. Further, in this configuration the top assembly 102 may be easily removed from the base 104 wherein the circular extrusions of the driver 210 may move axially away from the circular indentations along the rotation axis 208 to separate the driver from the inner part as the top assembly 102 is removed. When the driver 210 is coupled to the inner part 206 with the corresponding features 214 rotation of the driver 210 causes rotation of the inner part 206.

The needle 204 may be sufficiently bendable or deformable to allow the needle 204 to bend within the cavity 202. More specifically, the base may have a cylindrical wall 216 that defines a perimeter of the cavity 202. In a retracted position, the needle 204 may be substantially positioned within the cavity 202 wherein the needle 204 partially follows the contour of the inner surface of the cylindrical wall 216.This orientation of the needle 204 is illustrated in FIG. 2 as if the needle 204 were positioned in the cavity 202. In one aspect of this disclosure, the needle 204 has material properties that allow the needle 204 to bend under a load but otherwise maintain a substantially linear orientation. That is to say, if the needle 204 was not positioned within the cavity 202 and bending along the cylindrical wall 216 it would be substantially straight.

The base 104 may also have an insertion angle component 218 coupled thereto or formed therein. The insertion angle component 218 may have a guide channel therein that directs the bendable needle 204 from the cavity 202 out of the base 104 through a surface plane 402 (see FIG. 4). In one aspect of this disclosure, the insertion angle component 218 may deflect or bend the needle 204 into an orientation that provides a preferred entry angle for the needle in an extended position.

The insertion angle component 218 may be selectively replaceable within the base 104 wherein different insertion angle components 218 provide different angles of insertion. In this configuration, the manufacturer, health care provider, or user may select the insertion angle component 218 that provides the ideal insertion angle for the needle 204 in a given situation. In an alternative embodiment, the insertion angle component 218 is moulded into the base 104 during manufacturing and the insertion angle is pre-set and not adjustable.

Figure 3A:
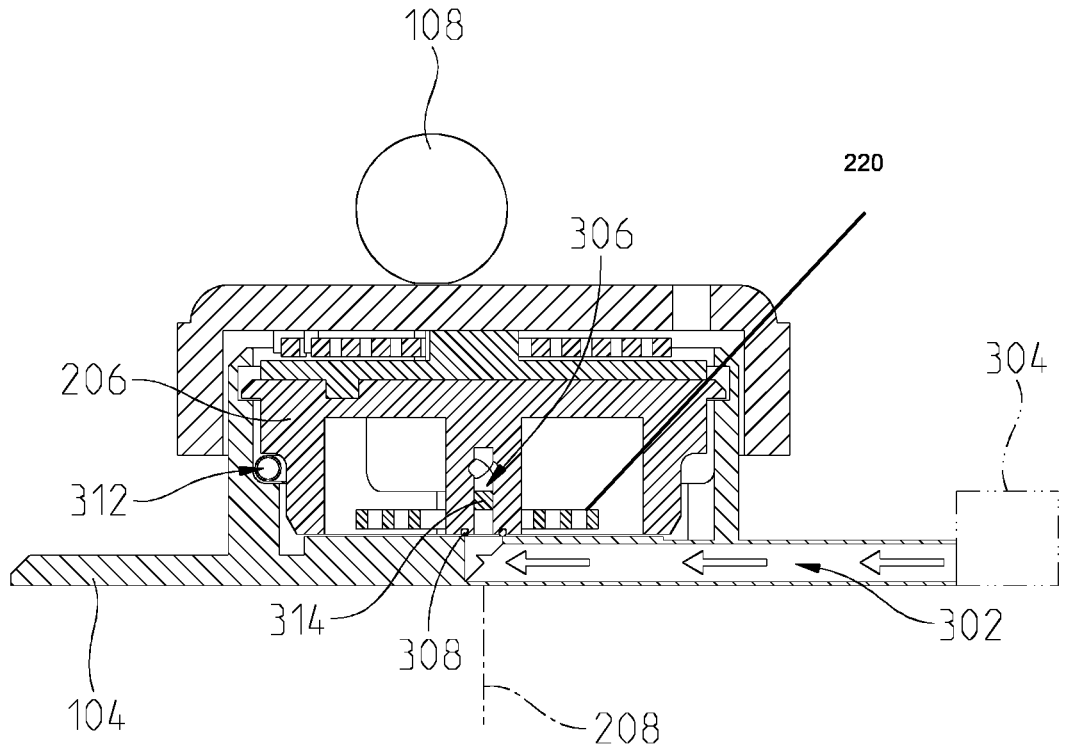
FIG. 3a is a section view of the inserter assembly of FIG. 1.
Figure 3B:
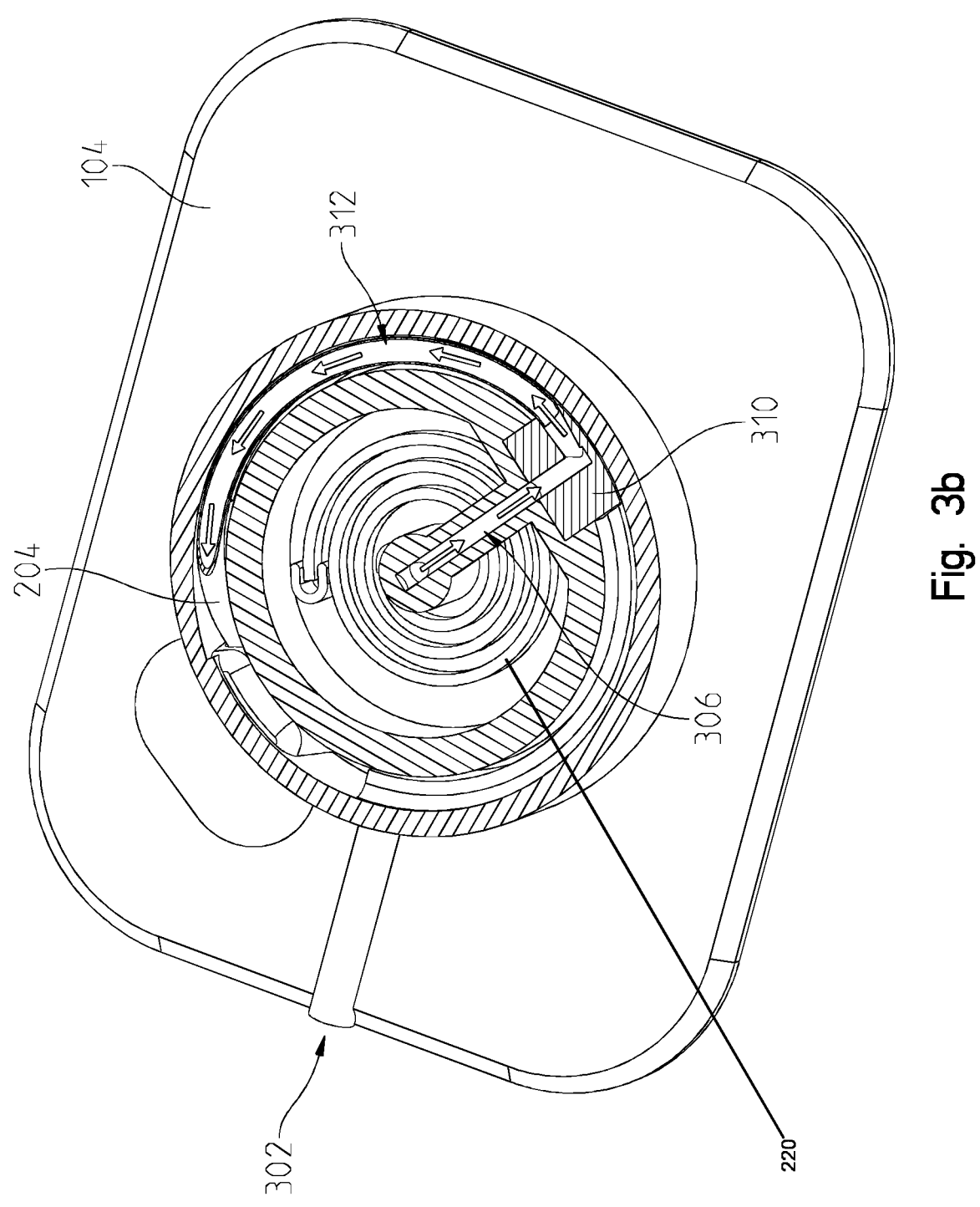
FIG. 3b is another section view of the inserter assembly of FIG. 1.

Referring now to FIGS. 3a and 3b, section views of the inserter assembly 100 are illustrated to show fluid channels of the inserter assembly 100. FIG. 3a illustrates a section view through the rotation axis 208 and a base fluid channel 302. The base fluid channel 302 may be a fluid channel defined by the base 104 that extends radially from the rotation axis 208 to a coupler 304. The coupler 304 may be sized to be coupled to a fluid source to fluidly couple the fluid source to the base fluid channel 302. The base fluid channel 302 may extend radially inwardly towards the rotation axis 208 until it is defined partially along the rotation axis 208. Further, the base fluid channel 302 may extend axially towards the inner part 206 about a central orifice.

The inner part 206 may have a corresponding inner fluid channel 306 that is fluidly coupled to the base fluid channel 302 at the central orifice. More specifically, a circular seal 308 may be positioned around the central orifice to fluidly seal the base fluid channel 302 to the inner fluid channel 306. In this configuration, the inner fluid channel 306 may remain fluidly coupled to the base fluid channel 302 regardless of the rotation angle of the inner part 206 relative to the base 104.

Referring to FIG. 3b, a section view through an upper part of the inner fluid channel 306 is illustrated. As illustrated in FIG. 3b, the inner fluid channel 306 may extend axially away from the base 104 for a length and then extend radially away from the rotation axis 208 towards a needle coupling component 310. The needle coupling component 310 may be a material that provides an interface to fluidly couple the inner fluid channel 306 to a needle fluid channel 312. In one aspect of this disclosure, the needle 204 may be moulded into the needle coupling component 310 to ensure fluid coupling between the needle fluid channel 312 and the needle coupling component 310. Further, a seal or the like may be positioned between the inner fluid channel 306 and the needle coupling component 310 to fluidly seal passages in the needle coupling component 310 to the inner fluid channel 306.

In one embodiment considered herein, one or more filter 314 may be positioned within a fluid channel between the coupler 304 and the distal tip 406 of the needle 204. The filter may be positioned to filter the fluid passing through the fluid channels 302, 306, 312 to remove impurities in the fluid or otherwise prepare the fluid to be introduced into the soft tissue of a user. In one example, the filter 314 at least partially filters one or more of phenol and meta-cresol residuals from fluid passing there through. However, other types of filters are also considered herein for filter 314.

In the configurations illustrated in FIGS. 3a-3b, fluid provided to the base fluid channel 302 from the coupler 304 will be directed to the inner fluid channel 306, through the needle coupling component 310, and into the needle fluid channel 312. Once in the needle fluid channel 312, the fluid will move towards the distal tip 404 of the needle 204 to be administered. In other words, the inserter assembly 100 may be fluidly coupled to a fluid source to deliver fluid through the needle 204. In one aspect of this disclosure, the fluid source can be a reservoir having a pump that provides fluid to the fluid channel 302 via a motorized pump (i.e., an electrically driven pump or a pressure driven pump through either gravity or over pressure containers) or a manual pump (i.e., like syringes) among other things.

Figure 4:
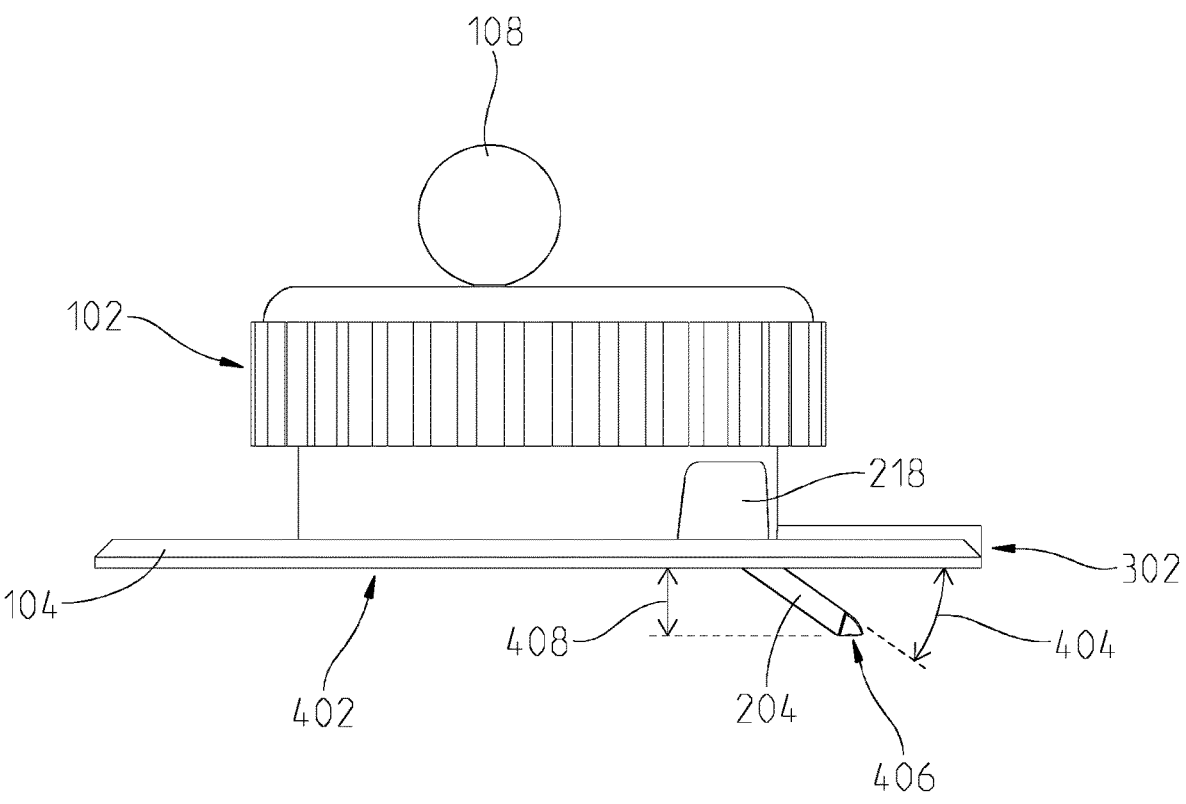
FIG. 4 is a side view of the inserter assembly of FIG. 1 in an extended position.

Referring now to FIG. 4, the inserter assembly 100 is illustrated in an extended position 400 wherein the needle 204 is at least partially extended past a surface plane 402 of the base 104. As the needle 204 extends from the insertion angle component 218, it returns to a substantially straight configuration. Further, the insertion angle component 218 may dictate an insertion angle 404 of the needle 204. The desired insertion angle may be different for different applications or users of the inserter assembly 100. As such, the insertion angle 404 of the same needle 204 may be substantially controlled by the insertion angle component 218. As discussed herein, the insertion angle component 218 may be interchangeable to produce different insertion angles 404. Further, the insertion angle component 218 may be formed with the base 104 and pre-set during manufacturing.

Figure 5:
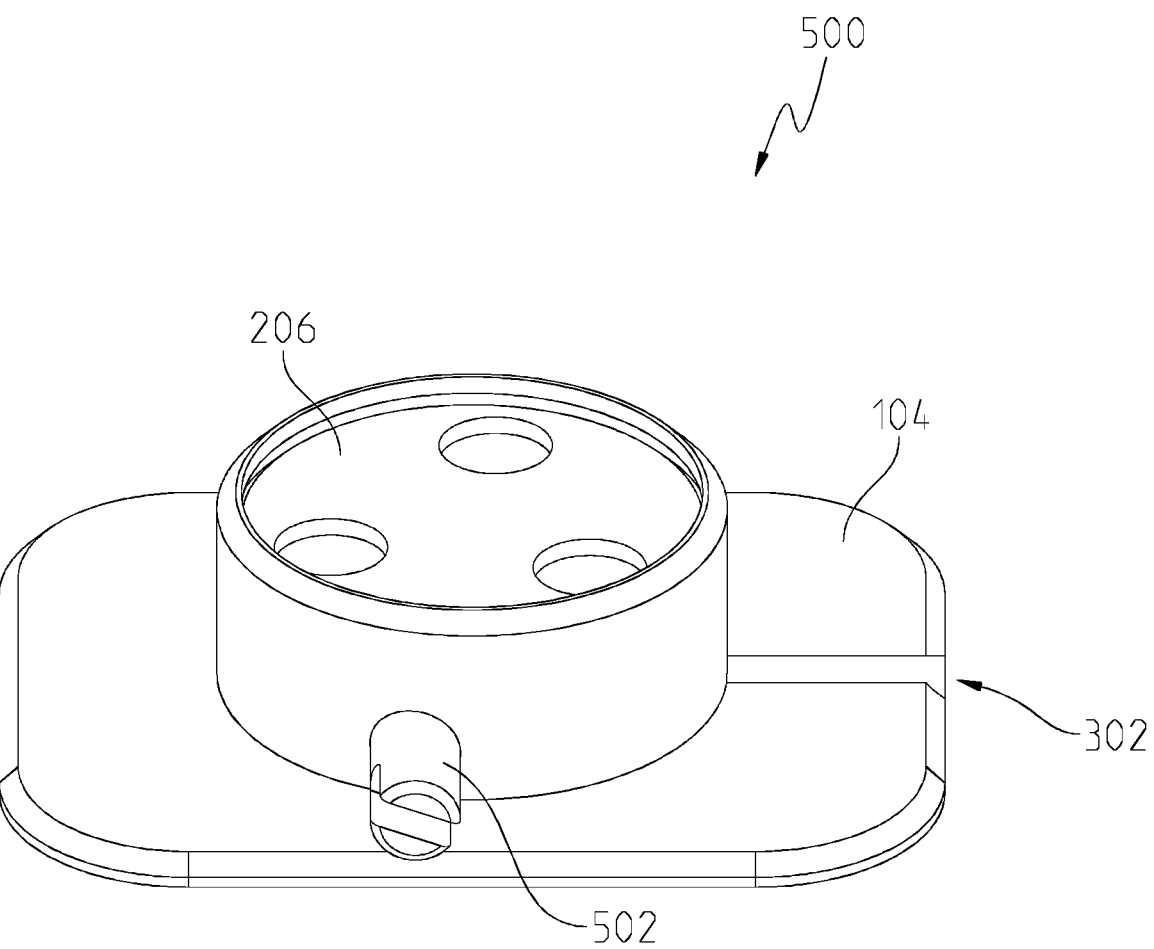
FIG. 5 is an elevated perspective view of another embodiment of an inserter device having a movable insertion angle component.

In yet another embodiment of an inserter assembly 500 illustrated in FIG. 5, a movable insertion angle component 502 may extend from the cylindrical wall 216 of the base 104 into the cavity 202 of the base 104 to selectively manipulate the insertion angle 404 of the needle 204. This embodiment 500 may be substantially the same as the embodiment described with reference to FIGS. 1-4 except it has the movable insertion angle component 502 instead of the insertion angle component 218. The movable insertion angle component 502 may be rotatable by a user to manipulate a corresponding channel through which the needle 204 must travel before exiting the base 104. In this configuration, the movable insertion angle component 502 may be engaged by the user to alter the insertion angle 404 of the needle 204.

In the embodiment with the movable insertion angle component 502, the insertion angle 404 may be adjustable to anything at or between about ninety degrees to less than twenty degrees. Alternatively, the insertion angle component 218 may be manufactured to provide an insertion angle 404 of anything at or between about ninety degrees to less than twenty degrees. In one aspect of this disclosure, the insertion angle 404 may be pre-set to about thirty degrees.

In another aspect of this disclosure, an insertion depth 408 may be selectable by the user as well. More specifically, a rotation angle of the inner part 206 from the retracted position (i.e., FIG. 3a) to the extended position (i.e., FIG. 4) may control the insertion depth 408 of the needle 204. In other words, a comparatively larger rotation angle of the inner part 206 will have a greater insertion depth 408 than a comparatively smaller rotation angle. Accordingly, in one embodiment considered herein, the rotation angle of the inner part 206 may be selectively altered to modify the insertion depth 408. In one example of this disclosure, the insertion depth 408 may be pre-set to about three to four millimetres. However, other embodiments considered herein include insertion depths greater than four millimetres or less than three millimetres.

Figure 8A:
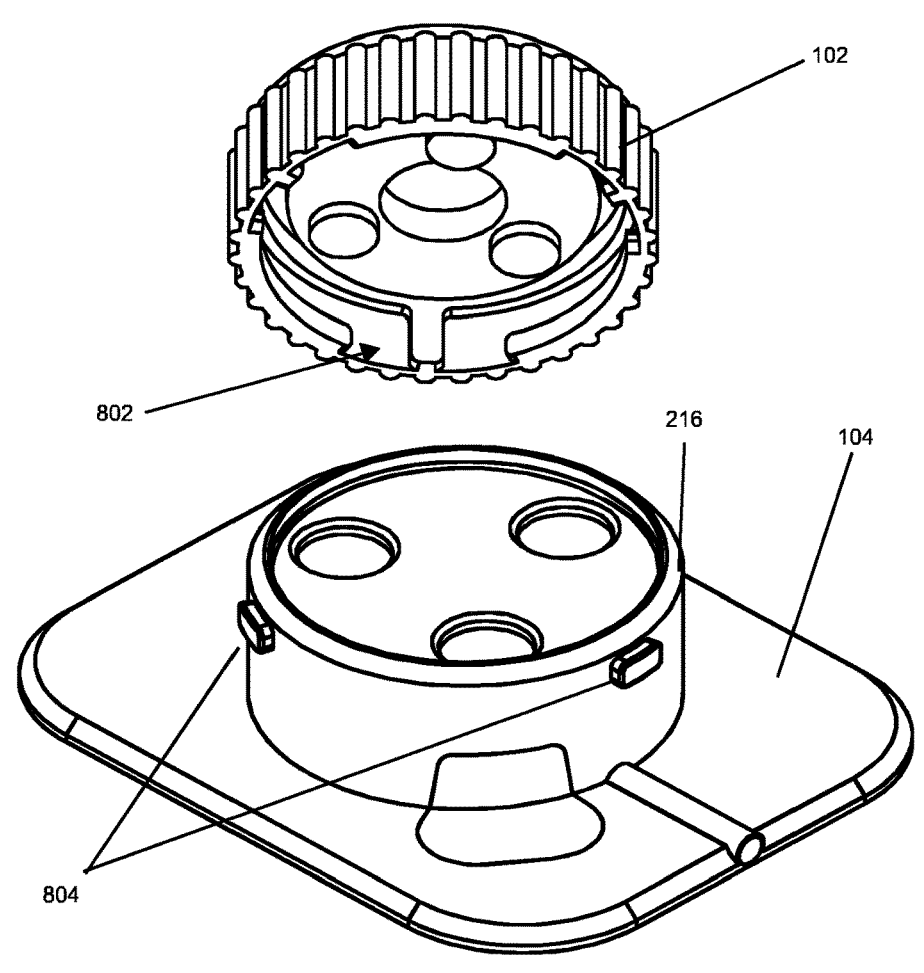
FIG. 8a is an elevated expanded view of another embodiment of an inserter assembly.
Figure 8B:
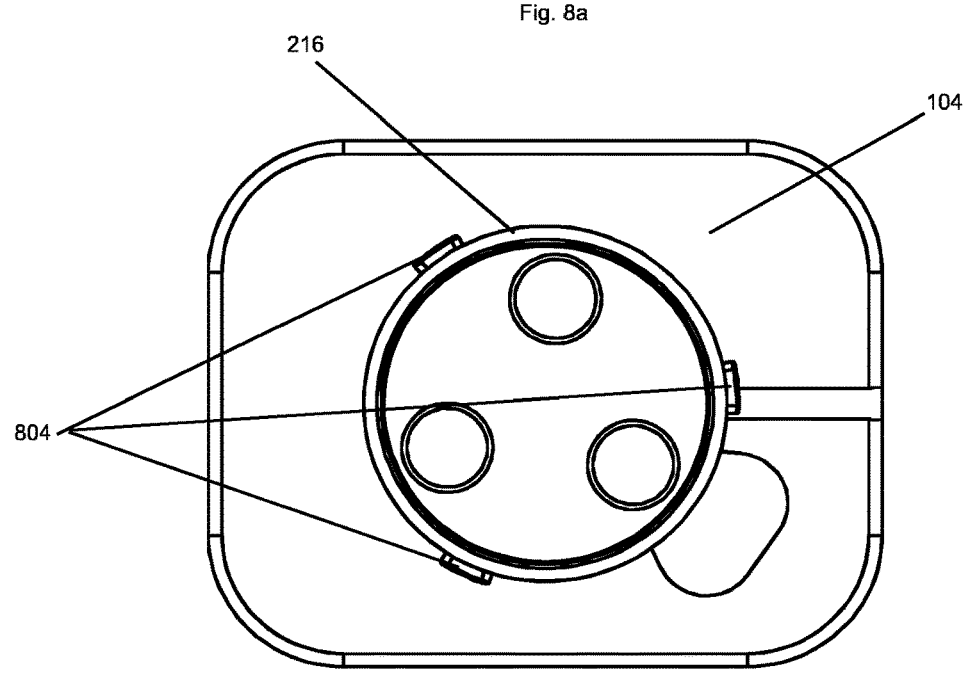
Figure 9:
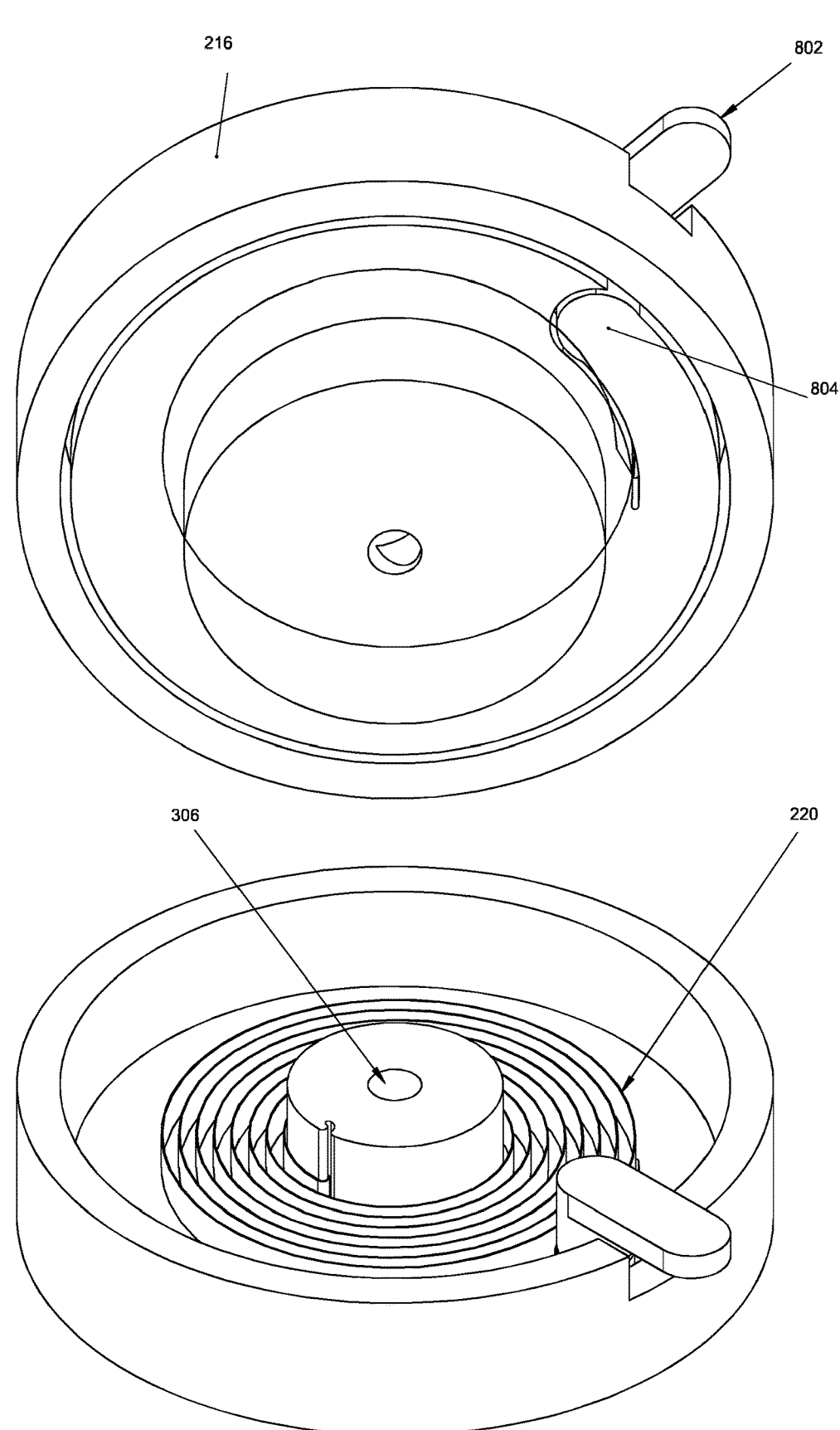
FIG. 9 is one embodiment of an inserter assembly having an activator for transitioning the needle from the extended position to the retracted position.

Referring now to FIGS. 8a and 8b, the top assembly 102 may be selectively removed from the base 104. More specifically, the top assembly 102 may be friction fit, clipped, or otherwise removably coupled to the base 104 wherein the corresponding features 214 of the inner part 206 and the driver 210 are aligned to rotationally couple the driver 210 to the inner part 206. More specifically, the top assembly 102 may have coupling grooves 802 that correspond with coupling pegs 804 on the base 104. The grooves 802 may be formed on a radially inner surface of the top assembly 102 and the pegs 804 may be formed on the radially outer portion of the cylindrical wall 216. Alternatively, the pegs could be defined from the top assembly 102 and the grooves could be formed in the cylindrical wall 216. Regardless, the top assembly 102 may be selectively coupled to the base 104 by positioning the pegs 804 in the grooves 802 and rotating the top assembly 102 to position the pegs 804 along a portion of the grooves 802 that to not allow substantial axial movement of the top assembly 102 away from the base 104. In this configuration, the driver 210 may be rotationally coupled to the inner part 206 via the corresponding features 214. Further, the top assembly 102 may be removed from the base 104 by rotating the top assembly so the pegs 804 can slide axially along the grooves 802 to allow the top assembly 102 to separate from the base 104.

Figure 6:
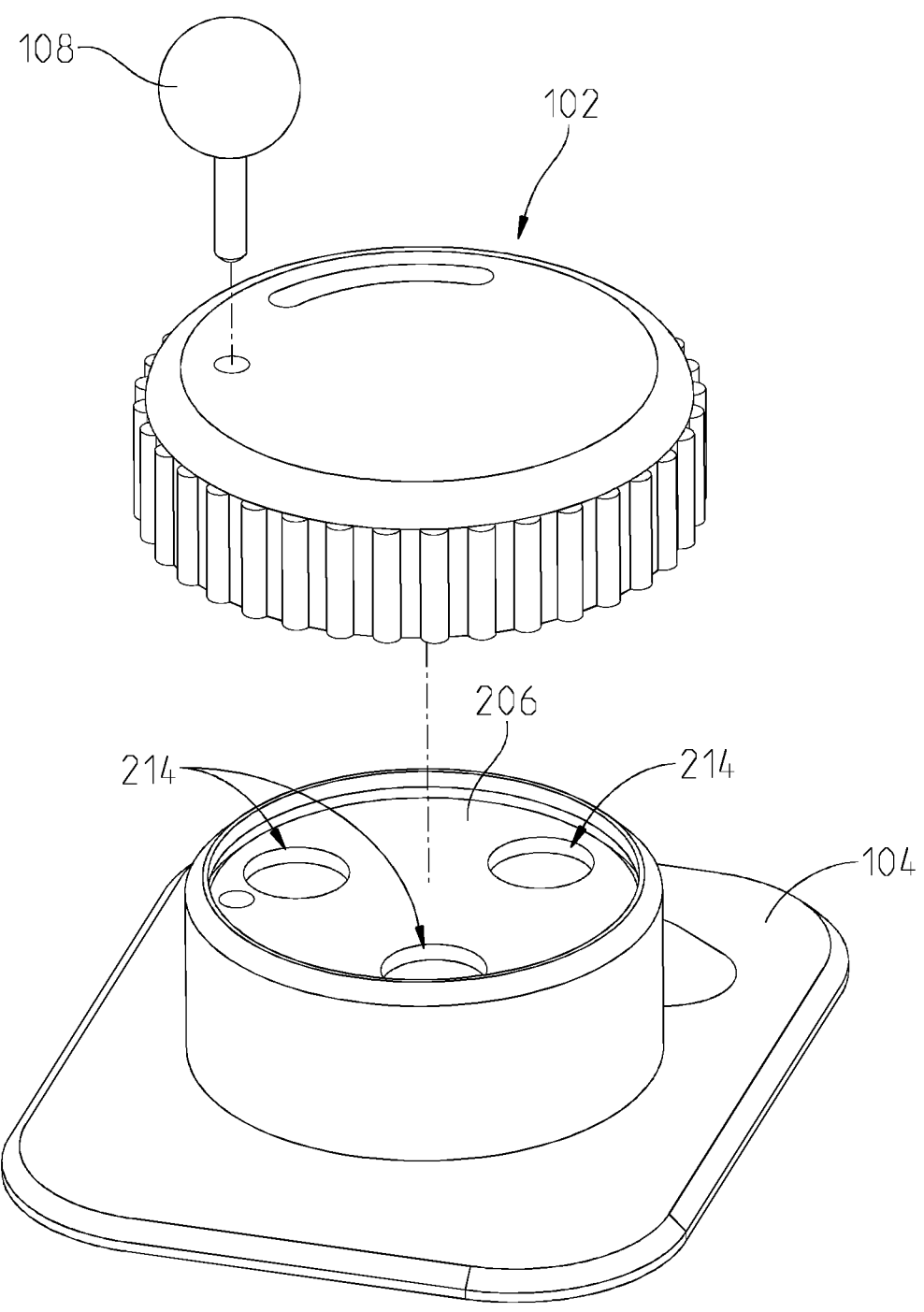
FIG. 6 is an elevated perspective view of the inserter assembly of FIG. 1 with a top assembly partially removed.

When the top assembly 102 is coupled to the base 104 and the inner part 206 to the driver 210, after the release mechanism 108 is released and the inner part 206 rotates the needle to the extended position. The top assembly 102 may then be removed from the base 104 as illustrated in FIG. 6. In this configuration, the top assembly 102 is removed when not needed (i.e., after the needle 204 has transitioned to the extended position) to provide a lighter and smaller inserter assembly.

In another aspect of this disclosure, the inserter assembly 100 may allow the needle 204 to transition from the extended position to the retracted position. More specifically, a return spring 220 may be positioned between the inner part 206 and the base 104 to provide a biasing force to the inner part 206 towards the retracted position. When the user wants to retract the needle 204, they may engage an activator 802 to release a lock pin 804 to thereby release the inner part 206 to rotate towards the retracted position. Once the lock pin 802 releases the inner part 206, the return spring 220 may provide a supplemental force returning the needle to the retracted position.

Figure 7:
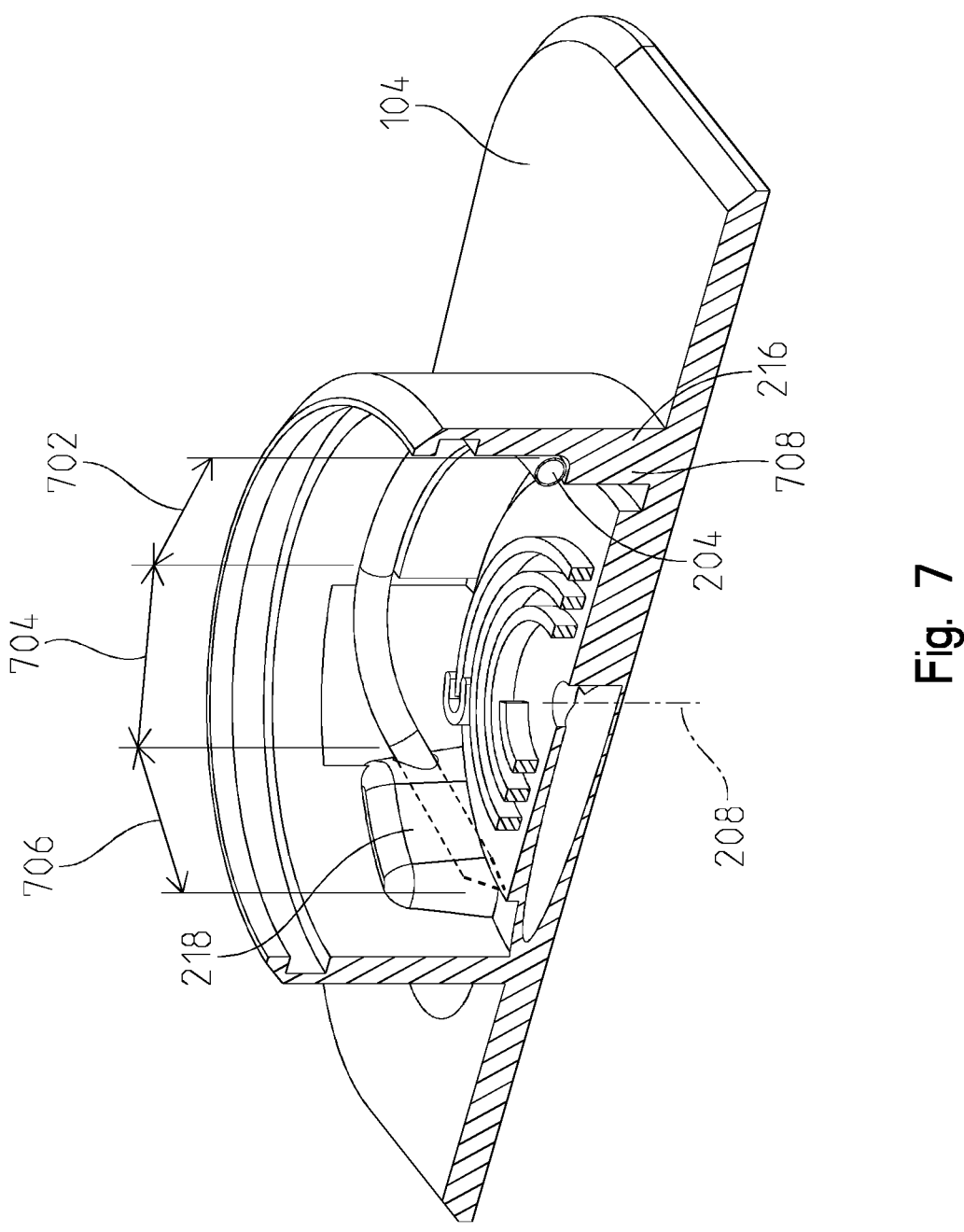
FIG. 7 is another section view of the inserter assembly of FIG. 1.

The bending, deflection, and/or deformation of the needle 204 in the base 104 is illustrated in the section view of FIG. 7 with the inner part 206 removed. More specifically, the needle 204 is illustrated having three different sections 702, 704, 706 of orientation. More specifically, in the first section 702 the needle 204 may be positioned between a shelf 708 defined in the inner portion of the cylindrical wall 216 of the base 104 and the inner part 206 (inner part 206 not illustrated in FIG. 7). In the first section 702, the needle 204 may maintain a substantially arc-shaped profile as it bends along the interior profile of the cylindrical all 216. However, as the needle 204 enters the second section 704, it may bend towards the insertion angle component 218 and alter the orientation of the needle 204 relative to the first section 702. In the second section 704, the shelf 708 may terminate allowing the needle 204 to be deflected towards the insertion angle component 218.

The third section 706 is in the insertion angle component 218. The third section 706 may have a substantially linear through hole defined through the insertion angle component 218 to thereby provide a linear exit for the needle 204. As discussed herein, the insertion angle component 218 may alter the insertion angle 404 of the needle 204. In this embodiment, the insertion angle 404 may be dictated by the angle of the linear through hole through the insertion angle component 218. Regardless, once the needle 204 exits the insertion angle component 218 it will retain a substantially linear orientation. In other words, the needle 204 may transition through three separate orientations before exiting the insertion angle component 218.

As discussed herein, the needle 204 is progressed through the sections 702, 704, 706 as the inner part 206 rotates about the rotation axis 208. From the perspective of FIG. 7, as the inner part 206 rotates in a counter clockwise direction about the rotation axis 208, the needle 204 will be pushed by the inner part 206 to be forced through the insertion angle component 218 into the extended position. Alternatively, the inner part 206 may rotate in the clockwise direction about the rotation axis 208 from the perspective of FIG. 7 to pull the needle 204 through the insertion angle component 218 into the retracted position.

In use, the inserter assembly 100 may have a top assembly 102 with a pre-loaded spring 212 and an adhesive patch or the like on the base 104 around the surface plane 402. The inserter assembly 100 may be in the retracted position and be coupled to a user's skin through the adhesive patch. When coupled to the user's skin, the surface plane 402 is substantially adjacent to the user's skin. Once positioned on the user's skin, the release mechanism 108 may be selectively removed by the user, healthcare provider, or other personnel. The release mechanism 108 may be pulled from through-holes in the lid 106 and driver 210 to thereby free the driver 210 to rotate relative to the lid 106.

Once the release mechanism 108 is removed, the spring 212 rotates the driver 210, and in turn the inner part 206 coupled thereto through the corresponding features 214, to transition the needle 204 from the retracted position (see FIG. 3a) to the extended position (see FIG. 4). As the inner part 206 rotates, the needle 204 rotates therewith feeding the distal tip 406 through the insertion angle component 218 and into the user's soft tissue. The insertion angle component 218 deflects the needle 204 to have the desired insertion angle 404 and the rotation angle of the inner part 206 may control the insertion depth 408. As the needle 204 extends into the user's soft tissue, the portion of the needle 204 entering the soft tissue retains a substantially linear orientation. Once in the extended position, the user, healthcare provider, or other personnel may remove the top assembly 102 to reduce the size and weight of the device.

The user, healthcare provider, or other personnel may selectively retract the needle 204 from the extended position to the retracted position by rotating the inner part 206 in the opposite direction as when transitioned to the extended position. In one example, a spring may provide a springe force on the inner part towards the retracted position and the user may selectively release the inner part to allow the spring to retract the needle 204 into the retracted position.

In another example of this disclosure, the top assembly 102 may act as a key for extending or retracting the needle 204. More specifically, the base 104, inner part 206, and needle 204 may be coupled to a user via an adhesive patch or the like. The top assembly 102 may then be manipulated into a loaded position with the release mechanism engaged to retain the loaded configuration. In one example, the top assembly 102 may be loaded by rotating the driver 210 relative to the lid 106 until the release mechanism can engage a catch in the driver 210 to maintain the loaded position. Once loaded, the top assembly can be positioned on the base wherein the corresponding features 214 of the inner part 206 align with the driver 210 such that the inner part 206 and driver 210 become rotationally fixed relative to one another. The top assembly 102 may be released by removing the release mechanism 108 to transition the needle 204 from the retracted position to the extended position.

In another aspect of this disclosure, a substantially similar process may be implemented as described above for retracting the needle 204. More specifically, the top assembly 102 may be loaded in a retracted configuration and positioned over the base 104. Then, the release mechanism 108 may be released to allow the drive 210 to rotate the inner part 206 towards the retracted position.

In another embodiment considered herein, a rotary actuator may rotate the inner part 206 relative to the base 104 to transition the needle 204 from the retracted position to the extended position. More specifically, a rotary actuator may be coupled to the base 104 such that movement of the rotary actuator causes rotation of the inner part 206 relative to the base 104. In one example, the rotary actuator may be an electric motor coupled to gears that engage the inner part 206 to selectively rotate the inner part 206 as the motor is powered to transition the needle 204 between the retracted and extended positions.

Figures 10A, 10B:
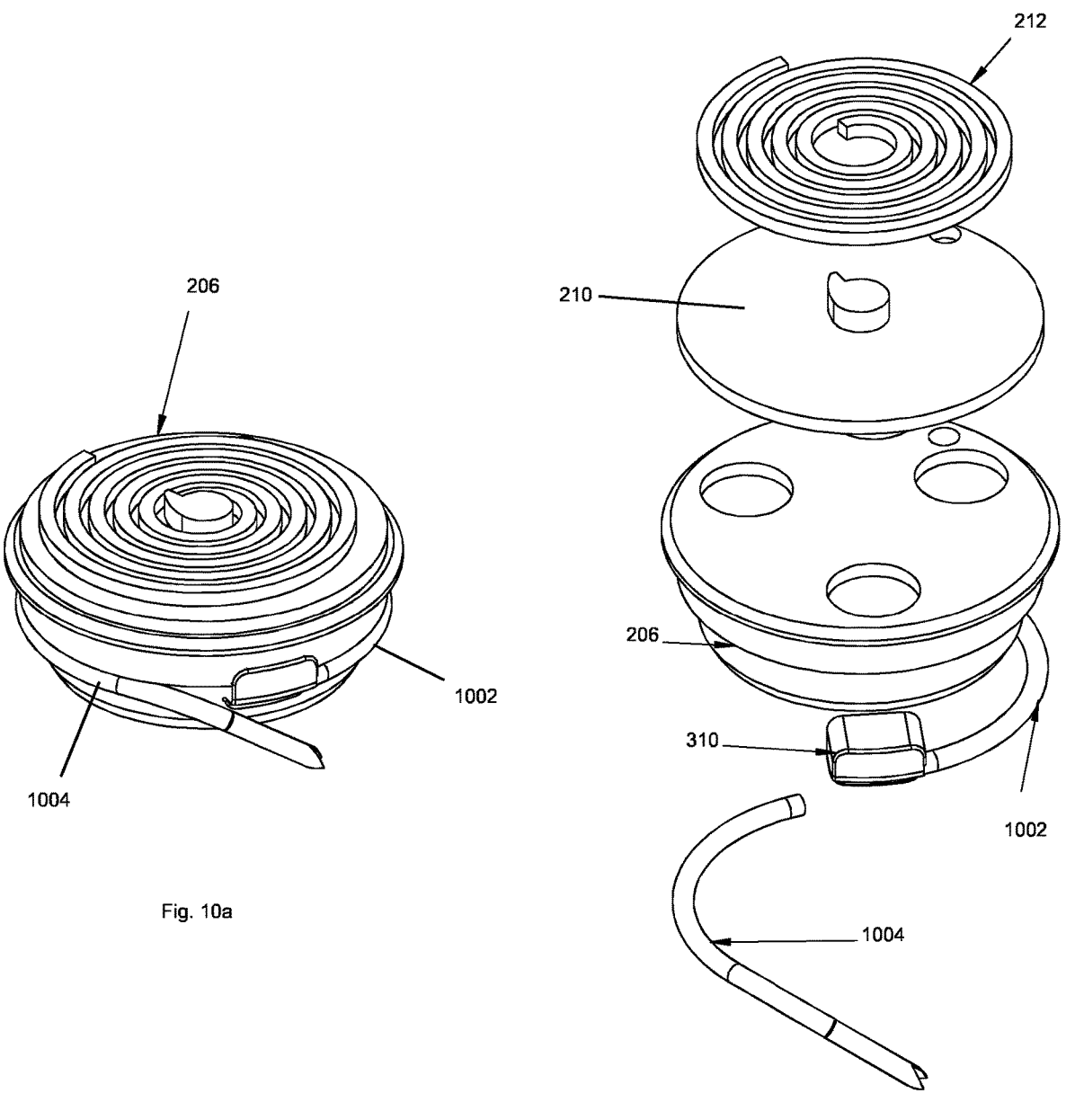
FIGS. 10a-10b illustrate another embodiment of an inserter assembly having two needles.

In yet another embodiment of this disclosure illustrated in FIGS. 10a and 10b, the inner part 206 may have fluid channels directed towards two separate needles 1002, 1004. Each needle 1002, 1004 may be coupled the inner part 206 substantially one-hundred and eighty degrees offset from one another about the rotation axis 208. In this configuration, the needles 1002, 1004 may extend down towards the surface plane 402 in substantially the same way as discussed herein with reference to FIGS. 1-7. That is, the second needle 1004 may be a substantially mirrored configuration as the needle 204 and corresponding components discussed herein. In this configuration, rotation of the inner part 206 may transition both the needles 1002, 1004 between the retracted position and the extended position. Further, two separate base fluid channels may be defined in the base 104 to allow each needle 1002, 1004 to be fluidly coupled to a separate fluid source. Other than having a second needle 1004, the embodiment of FIGS. 10a and 10b may function substantially similarly as the other embodiments shown and discussed herein.

While embodiments incorporating the principles of the present disclosure have been described hereinabove, the present disclosure is not limited to the described embodiments. Instead, this application is intended to cover any variations, uses, or adaptations of the disclosure using its general principles. Further, this application is intended to cover such departures from the present disclosure as come within known or customary practice in the art to which this disclosure pertains and which fall within the limits of the appended claims.

The invention claimed is:

1. An inserter assembly, comprising:
   a base;
   a needle;
   an inner part configured to selectively transition the needle from a retracted position substantially within the base to an extended position where at least a portion of the needle extends outside of the base;
   an insertion angle component; and a base fluid channel defined partially in the base and an inner fluid channel defined in the inner part, wherein, as the inner part transitions the needle from the retracted position to the extended position, the needle is at least partially deflected by the insertion angle component, wherein the base fluid channel is fluidly coupled to the inner fluid channel, wherein the inner fluid channel is fluidly coupled to a needle fluid channel, and wherein fluid from the base fluid channel is directed partially through the inner fluid channel of the inner part and into the needle fluid channel of the needle regardless of a rotation angle of the inner part relative to the base about a rotation axis.

2. The inserter assembly of claim 1, further wherein the inner part is rotationally coupled to the base about the rotation axis and the inner part is coupled to the needle such that rotation of the inner part about the rotation axis moves the needle about the rotation axis.

3. The inserter assembly of claim 1, further wherein the needle is elastically deformable to fit within the base and deflect through contact with the insertion angle component as the needle transitions from the retracted position to the extended position, wherein the needle maintains a substantially linear configuration as it extends outside of the base.

4. The inserter assembly of claim 1, further comprising a top assembly that is selectable to transition the needle from the retracted position to the extended position, wherein the top assembly comprises a lid, a driver selectively rotatable relative to the lid, a release mechanism, and a spring positioned between the driver and the lid, the spring being loaded to provide a rotation force on the driver relative to the lid and the release mechanism being selectively coupled to the driver to prevent the driver from rotating relative to the lid.

5. The inserter assembly of claim 4, wherein the top assembly is removable from the base and the inner part.

6. The inserter assembly of claim 1, further wherein the insertion angle component is removable from the base and a plurality of different insertion angle components are coupleable to the base to provide a selectable insertion angle of the needle in the extended position, each one of the plurality of different insertion angle components providing a different insertion angle.

7. The inserter assembly of claim 1, wherein the insertion angle component is movable to alter an insertion angle of the needle in the extended position.

8. The inserter assembly of claim 1, wherein a rotary actuator rotates the inner part relative to the base to transition the needle from a retracted position to an extended position.

9. The inserter assembly of claim 1, further comprising a second needle coupled to the inner part wherein the inserter assembly transitions the second needle from a retracted position to an extended position wherein at least a portion of the second needle extends outside of the base.

10. An inserter assembly, comprising:

a base;

a needle;

an inner part configured to selectively transition the needle from a retracted position substantially within the base to an extended position where at least a portion of the needle extends outside of the base;

an insertion angle component; and a top assembly that is selectable to transition the needle from the retracted position to the extended position, wherein the top assembly comprises a driver, a lid, a release mechanism, and a spring positioned there between;

wherein, as the inner part transitions the needle from the retracted position to the extended position, the needle is at least partially deflected by the insertion angle component, and wherein the top assembly is removable from the base and the inner part.

11. An inserter assembly, comprising:

a base;

a needle;

an inner part configured to selectively transition the needle from a retracted position substantially within the base to an extended position where at least a portion of the needle extends outside of the base; and an insertion angle component, wherein, as the inner part transitions the needle from the retracted position to the extended position, the needle is at least partially deflected by the insertion angle component, and wherein the insertion angle component is removable from the base and a plurality of different insertion angle components are coupleable to the base to provide a selectable insertion angle of the needle in the extended position, each one of the plurality of different insertion angle components providing a different insertion angle.

* * * * *